United States Patent [19]

Cosman

[11] 4,353,371
[45] Oct. 12, 1982

[54] LONGITUDINALLY, SIDE-BITING, BIPOLAR COAGULATING, SURGICAL INSTRUMENT

[76] Inventor: Eric R. Cosman, 872 Concord Ave., Belmont, Mass. 02178

[21] Appl. No.: 190,301

[22] Filed: Sep. 24, 1980

[51] Int. Cl.³ ............................................. A61B 17/39
[52] U.S. Cl. ................................................ 128/303.17
[58] Field of Search .................... 128/303.13, 303.15, 128/303.17, 321, 322

[56] References Cited

U.S. PATENT DOCUMENTS 3,685,518  8/1972  Beurle et al. ................... 128/303.17
3,911,241  10/1975  Jarrard ............................ 128/303.17

FOREIGN PATENT DOCUMENTS 2415263  10/1975  Fed. Rep. of Germany ........................ 128/303.17

Primary Examiner—Lee S. Cohen
Attorney, Agent, or Firm—Richard J. Birch

[57] ABSTRACT

The present invention is a new kind of bipolar coagulating instrument which has special application in certain microsurgical or neurosurgical contexts in which one must grip and coagulate a web of tissue or membrane which is inside a deep surgical hole, and where the web hangs from the side wall of the hole and is in a plane perpendicular to the line of sight. The instrument must then be adapted to grip the hanging membrane with its tips and close down on the membrane in a direction which is parallel to the line of sight, and then apply a coagulating potential to its tips to coagulate the membrane. The invention then has a side-biting tips which close in a longitudinal direction, i.e. parallel to the line of sight or the distal axis of the instrument, and which has tips that are electrically insulated to become the two poles of the coagulating electric potential. Thus this longitudinally, side-biting, bipolar coagulating, surgical instrument is in marked contrast to conventional bipolar coagulating forceps, the tips of which always close in direction which is transverse, i.e. perpendicular, to the direction of line of sight or the distal axis of the instrument.

5 Claims, 7 Drawing Figures

LONGITUDINALLY, SIDE-BITING, BIPOLAR COAGULATING, SURGICAL INSTRUMENT

BACKGROUND OF THE INVENTION

The bipolar coagulating forceps is a common instrument in many branches of surgery, it being heavily used in microsurgery such as neurosurgery and eye surgery where pinpoint coagulation of small bleeding tissue or arteries is required. Bipolar forceps first appeared in the late 1950's and early 1960's, and now are commercially available from dozen's of manufacturers and their dealers. The world's leading manufacturers of bipolar forceps are: Radionics, Inc., Codman and Shurtleff, and Storz Instruments, of the USA; Aesculap Instruments, Karl Storz, and MET Fischer, of W. Germany. Bipolar forceps vary widely in shape and styles, but their functional geometry and means of actuation is always the same. FIG. 1 shows a typical example. They are like regular forceps except that the two forceps arms, 1 and 1', in FIG. 1, are electrically insulated from each other. When 1 and 1' are connected to a high voltage rf potential source 3, and when tips 2 and 2' of arms 1 and 1', respectively, encounter conductive tissue, then electric current heating of the tissue between 2 and 2' will occur. This results in desired coagulation. The arms 1 and 1' define a distal axis A—A' of the forceps. This might also be referred to as the longitudinal axis. The surgeon will direct the axis A—A' to the target, squeeze the arms 1 and 1' together, thus closing the tips 2 and 2' upon the tissue or artery to be coagulated. Once so closed, the surgeon will turn on the electric potential between 1 and 1', and thus between 2 and 2', thereby ohmically coagulating the targeted tissue. This technique and principle is described in detail in commercial brochures.

Note that we will refer to the distal end of an instrument as that which is directed at the patient or target, as the front end of the forceps, and the proximal end as that nearest the surgeon, as the handle end of the forceps. The distal axis A—A' of an instrument is approximately the direction in which its distal end points, as, for example, the direction that the distal arms of a forceps points toward the object it is to contact. Usually when a surgeon aims an instrument down a deep surgical hole to reach a target the distal axis of the instrument is approximately the axis of the surgical hole or the line of sight of the surgeon, especially if he is viewing the target through a surgical microscope. One might also refer to the distal axis of the instrument as the longitudinal axis, which also implies being along the direction that the elongated distal end of the instrument is pointing. An axis perpendicular to the line of sight could then be defined as being transverse to the line of sight.

For all bipolar forceps to date, their tips always close along a transverse direction that is a direction which is perpendicular to the distal axis A—A' of the forceps. Specifically, when the grips 4 and 4' of the forceps arms are squeezed together, then 4 and 4', 1 and 1', and 2 and 2' move together so that the tips 2 and 2' move along a line B—B' which, near the point of closure, is perpendicular to the axis A—A'. Thus B—B' might also be referred to as a transverse axis or direction relative to A—A'. The arms 1 and 1', including 2 and 2' and 4 and 4', are continuous metal conductors, and 1 and 1' are joined at their base by insulating element 5, so 1 and 1' are electrically isolated from each other. The shape of the arms 1 and 1' and their tips 2 and 2' and handles 4 and 4' may vary; i.e. 1 and 1' may have straight or bayonet shape; tips 2 and 2' may be straight bent, or curved up or down by 90°; but the basic forceps axis A—A' and perpendicularity of tip movement axis B—B' relative to A—A' is always present. So in cases where the surgeon is looking into a deep surgical hole, as shown in FIG. 2A, then the direction of the hole would be forceps axis A—A', and one can only close tips 2 and 2' on tissue to be coagulated in a direction B—B' perpendicular to A—A', i.e. perpendicular to the surgeon's line of sight. This is a severe restriction in certain surgical situations, as will be shown below.

DESCRIPTION OF THE INVENTION

Figure 1A:
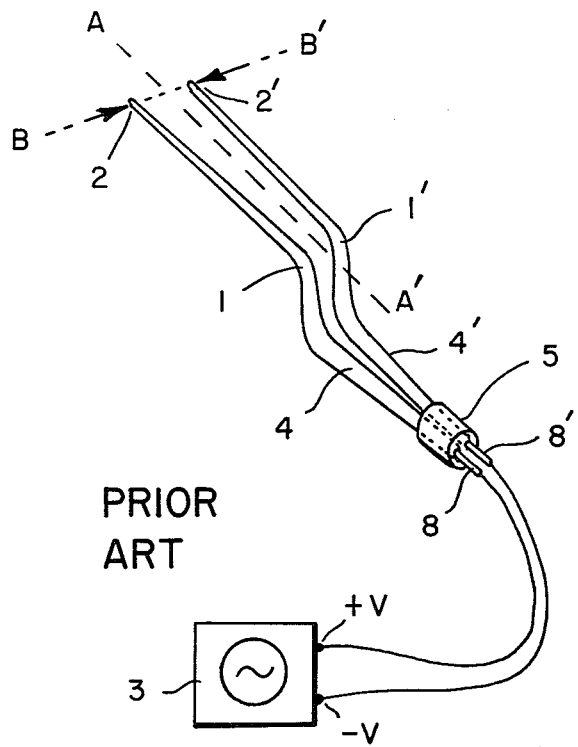
FIGS. 1A and B are perspective views of prior art bipolar coagulating forceps.
Figure 1B:
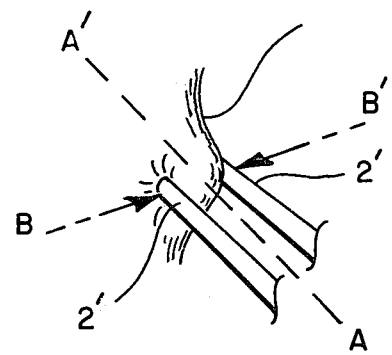
Figure 2A:
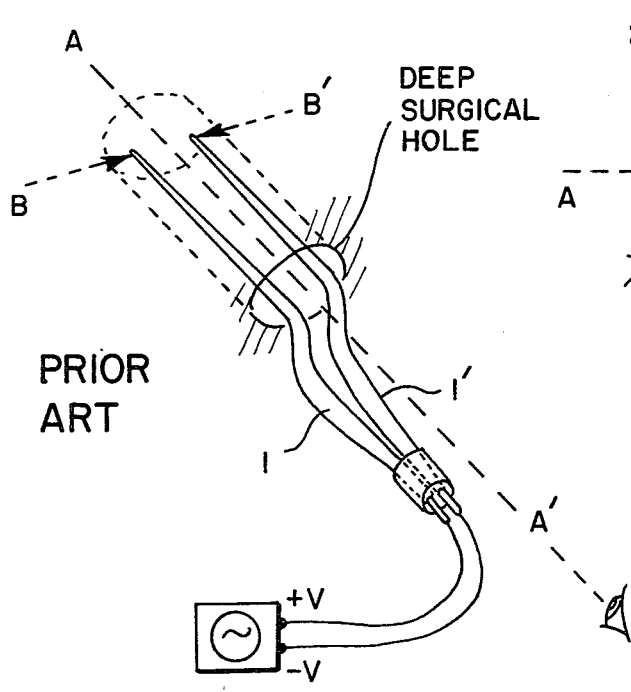
FIG. 2A shows the use of a prior art forceps of FIG. 1A.
Figure 2B:
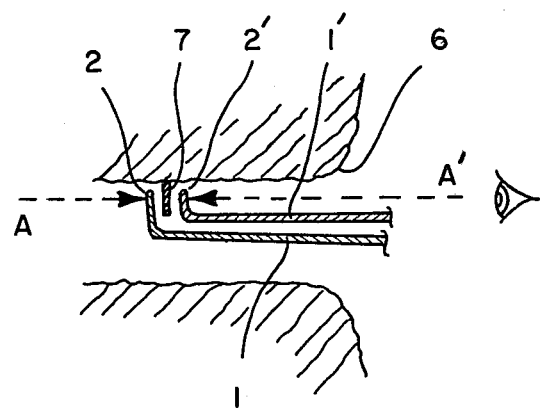
FIG. 2B is a cross-sectional view of the bipolar coagulating instrument in accordance with the invention in use.

The present invention relates to a new kind of bipolar coagulating device which enables a surgeon to close down on and coagulate tissue with the device's tips in a direction that is substantially in the same direction as i.e. parallel to, the distal axis of the device, that is along the surgeon's line of sight or along the axis of a surgical hole. FIG. 2B illustrates the problem. It shows a section view of a surgical hole 6 and a piece of tissue membrane 7 which is positioned perpendicular to the hole axis, A—A'. A common example is the dural membrane in a deep access hole to the hypophysis in neurosurgery. Ordinary bipolar forceps could not grap such a membrane since their closure direction B—B' would be parallel to the membrane. To coagulate 7, the device must have bipolar tips 2 and 2' which, at the limit of closure, close in a direction parallel to the surgical hole axis A—A'. That is, the device's tips must close in a direction parallel to the axis defined by its distal or projection end. This might also be described as a tip closure in the longitudinal direction. This closure should conveniently be effected by a squeezing or closing action of elements on the devices grip or handle end, i.e. the proximal end, although other actuations such as pushing on plungers or buttons are possible. The present invention has as an objective such a longitudinal, side-biting, bipolar coagulating capability.

Figure 3:
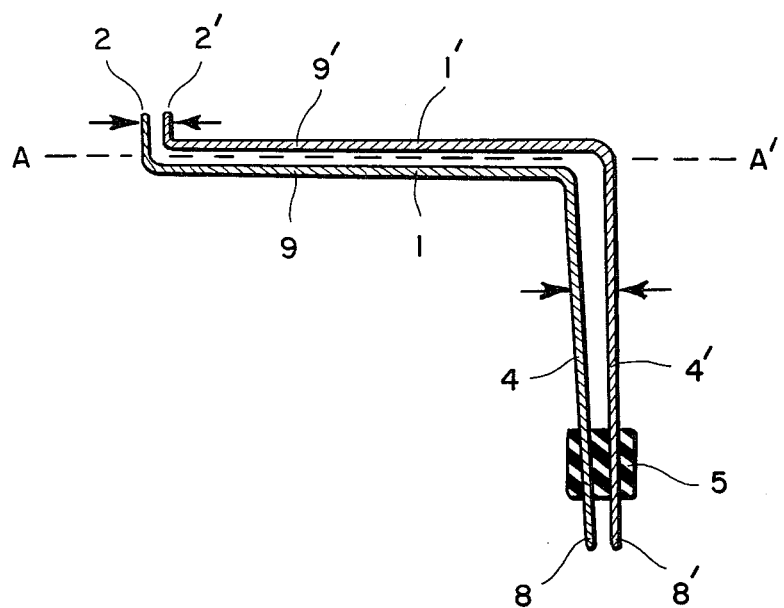
FIG. 3 is a cross-sectional view of the bipolar coagulating instrument in accordance with the invention.

FIG. 3 shows a means of enabling such a longitudinally side-biting bipolar coagulating instrument. Conductive elements 1 and 1' comprise tip ends 2 and 2', distal portions 9 and 9', handle or proximal portions 4 and 4', and electrode pins 8 and 8', respectively. Insulator 5 isolates them electrically. Pins 8 and 8' connect 1 and 1' to the coagulating potential. Portions 4 and 4' are bent at about 90° to 9 and 9', respectively, and 9 and 9' are sent at about 90° to 2 and 2', respectively, so that 2 and 2' are about parallel to 4 and 4'. Thus, when 4 and 4' are squeezed together (see the arrows in FIG. 3), 2 and 2' close in a direction which is parallel to portions 9 and 9'. The portions 9 and 9' would comprise the distal end of the instrument that would be inserted into the surgical hole and would be parallel to sight axis A—A' and thus the objective of FIG. 2B is achieved. The embodiment of FIG. 3 has the simplicity of just two metal bipolar elements 1 and 1' clamped by a simple insulating element, and yet it is conformally different from the usual bipolar forceps in that it enables the axial or longitudinal closing action which ordinary bipolar forceps cannot do. Note, elements 1 and 1' may be coated with an insulating material except for tip 2 and 2' to prevent any short circuits along their length.

Figures 4, 5:
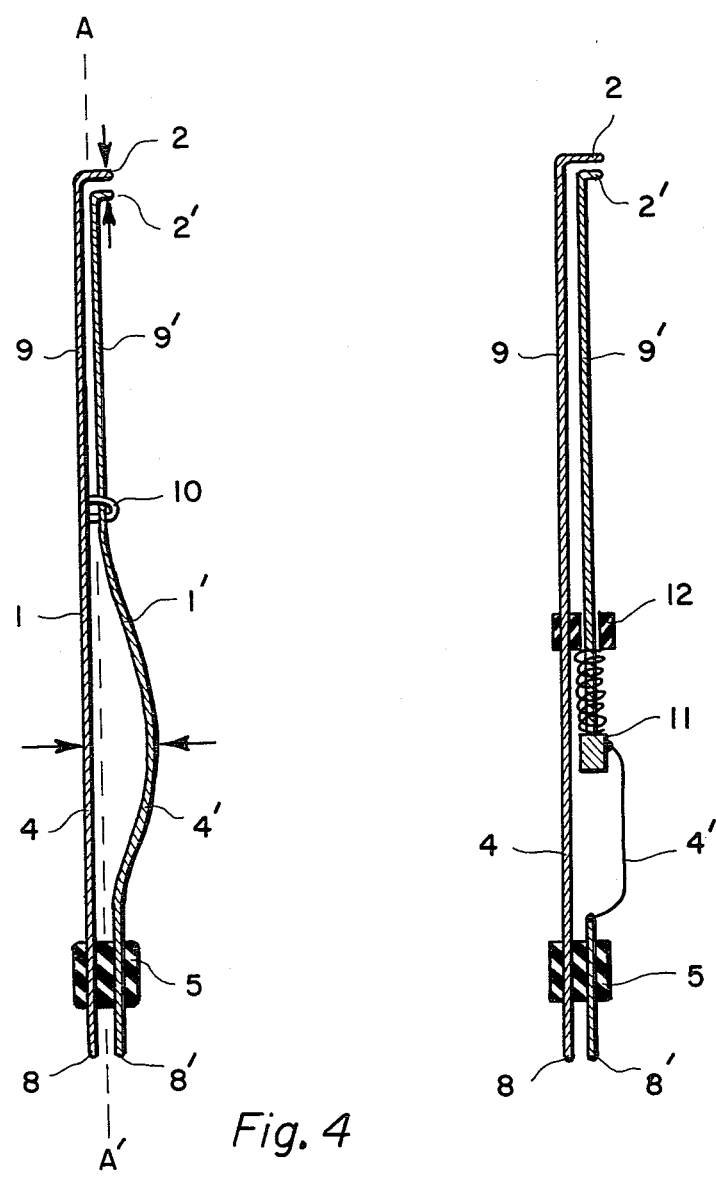
FIG. 4 is a cross-sectional view of another embodiment of the instrument in accordance with the invention.
FIG. 5 is a cross-sectional view of another embodiment of the instrument in accordance with the invention.

FIG. 4 illustrates another embodiment of the invention. Here 1' has a spring-metal, bowed-out portion near its proximal grip 4', such that, when 4 and 4' are squeezed together, then distal portions of 1 and 1', 9 and 9', displace parallel to each other, and tips 2 and 2' close parallel to the distal axis A—A' (see direction of arrows). Bipolar elements 1 and 1' may be insulated except for the bare tips 2 and 2', and a guide 10 will help keep 1 and 1' aligned. The same parallel closure action could be achieved by other means than the bowed metal portion of FIG. 4. For example, in FIG. 5, one could have a coiled spring-loaded plunger 9' with a push knob 11 at its proximal end. The knob may be pushed with a finger so that it will advance parallel to 9, and tip 2 and 2' will close in parallel to 9 or axis A—A'. Insulator 12 guides 9', and wire 4' electrically connects 9' to the proximal pin 8'.

Having described in detail various embodiments of my invention, it will now be apparent to those skilled in the art that numerous modifications can be made therein without departing from the scope of the invention as defined in the following claims.

What I claim and desire to secure by Letters Patent of the United States is:

1. A bipolar coagulating surgical instrument adapted for closing upon and coagulating tissue in a direction parallel to its distal axis, comprising:

a proximal portion having a proximal end and a distal portion having a distal end, the proximal portion being so adapted to be held when in use, the distal portion being so adapted to be directed toward the tissue to be coagulated when in use, and said distal portion being of elongated shape so that it can be directed into a deep surgical hole in the living body in order to reach a portion of tissue deep within the surgical hole and so that said distal portion defines approximately a distal axis of said surgical instrument, a first conductive element and a second conductive element which both extend from said proximal end to said distal end, means for electrically insulating at least a portion of said conductive elements with the tips of said conductive elements at said distal end being at least in part uninsulated and being the bipolar coagulating portion of said instrument, and the proximal ends of said conductive elements being adapted to be connected across a coagulating electric potential source when said instrument is in use, actuation means located at said proximal portion being so adapted and so cooperatively coupled to said two conductive elements that when said actuation means is pressed then said tips of said conductive elements will move relative to each other along a direction approximately parallel to the distal axis of said instrument, and said tips being so shaped that at least part of their uninsulated portions will close toward each other in such a way that said uninsulated tip portions can close upon each other and upon a plane which is oriented approximately perpendicular to said distal axis of said instrument, said conductive elements being so adapted to be electrically insulated from each other whenever said uninsulated portions of said tips of said conductive elements are not in contact with each other; whereby, when in use, said distal portion of said instrument can be inserted in to a deep surgical hole in the living body so that said distal axis of said instrument can be approximately aligned with the axis of said deep surgical hole, and, by pressing said actuation means, said uninsulated portions of said tips can be made to close upon a portion of membrane of tissue which hangs from the side walls of said deep surgical hole at a deep location in said surgical hole, said membrane being oriented in a plane that is perpendicular to said distal axis of said instrument, said uninsulated portions of said tips closing upon said portion of hanging membrane in a direction approximately parallel to said distal axis of said instrument; whereupon, when a coagulating electric potential is applied to said conductive elements, said membrane may be coagulated between said uninsulated portions of said tips.

2. The instrument of claim 1 wherein said actuation means comprises a curved element in said proximal portion of said instrument, the curved element being so adapted that when said actuation means is pressed said curved element becomes more straightened so that its length increases, said curved element being so cooperatively connected to at least one of said conductive elements that said length increase will give rise to said movement of said tips of said conductive elements relative to each other in a direction parallel to said distal axis and thus will give rise to the closure of said tips towards each other in a direction parallel to said distal axis.

3. The instrument of claim 2 wherein said curved element is part of said first conductive element and is so adapted that the curved portion of said curved element is a bowed out portion on the proximal portion of said instrument whereby when in use and when said instrument is being held by said proximal portion then said bowed out portion can be squeezed and thus straightened out relative to the rest of said proximal portion, thereby giving rise to said tip closure in said distal axis direction.

4. The instrument of claim 1 wherein said actuation means comprises a plunger means which is located in said proximal portion of said instrument, the plunger means being so mechanically coupled to said first conductive element that when said plunger means is pushed then said movement of said tips of said two conductive elements relative to each other will result.

5. A bipolar coagulating instrument adapted to close upon and coagulate tissue in a direction parallel to its distal axis, comprising:

a first elongated conductive element and a second elongated conductive element which are electrically isolated from each other with each element having a distal portion and distal end and a proximal portion and proximal end, said conductive elements being mechanically connected together by an insulating element located near the proximal end of each conductive element, the proximal portions being oriented in about the same direction from said insulating element so that said two proximal portions are adapted to be held by the surgeon during surgery, each of said conductive elements having about a right angle bend located between said proximal portion and said distal end with the portion of each of said conductive elements between said distal end and the bend in each respective conductive element being the distal portion of said respective conductive element and with the distal portions of said conductive elements being oriented in about the same direction so that said two distal portions define an approximate distal axis of said instrument such that in use said distal axis is directed toward the tissue to be coagulated, and so that when said two proximal portions are squeezed together with said insulating element acting as a pivot then said two distal portions move relative to each other in a direction approximately parallel to said distal axis, said conductive elements each having an uninsulated tip on its distal end, the distal tips of said conductive elements being so shaped that they will close upon each other in a direction parallel to said distal axis when said proximal portions are squeezed together, said conductive elements having a spring return action so that when they are not squeezed together then said uninsulated tips will separate, said conductive elements being adapted at their proximal ends to be connected to the poles of a coagulating electric potential; whereby, when said instrument is in use, said distal portions of said conductive elements are adapted to be inserted into a deep surgical hole in the living body with said distal axis of said instrument being approximately aligned with the axis of the deep surgical hole, and said uninsulated tips of said conductive elements can be closed upon a portion of a membrane of tissue which hangs from the sides of said deep surgical hole, at a deep location in said surgical hole, said membrane being oriented in a plane that is perpendicular to said distal axis of said instrument, and said tips of said conductive elements closing upon said portion of hanging membrane in a direction approximately parallel to the axis of said deep surgical hole; whereupon, when a coagulating electric potential is applied to said conductive elements, said membrane may be coagulated between said uninsulated tips.

* * * * *